US009956257B2

(12) United States Patent
Guthrie et al.

(10) Patent No.: US 9,956,257 B2
(45) Date of Patent: May 1, 2018

(54) CANOLA EXTRACTS CONTAINING HIGH LEVELS OF PHENOLIC ACIDS (71) Applicant: KGK SYNERGIZE, INC., London (CA)

(72) Inventors: Najla Guthrie, London (CA); Robert Allen Guthrie, London (CA)

(73) Assignee: KGK Science, Inc., London (CA)

( * ) Notice: Subject to any disclaimer, the term of this patent is extended or adjusted under 35 U.S.C. 154(b) by 448 days.

(21) Appl. No.: 14/812,207

(22) Filed: Jul. 29, 2015

(65) Prior Publication Data

US 2015/0328270 A1 Nov. 19, 2015

Related U.S. Application Data (63) Continuation of application No. 12/555,568, filed on Sep. 8, 2009, now Pat. No. 9,125,887, which is a continuation of application No. 11/260,758, filed on Oct. 27, 2005, now abandoned.

(51) Int. Cl.
*A61K 36/00* (2006.01)
*A61K 36/31* (2006.01)
*A61K 31/192* (2006.01)
*A61K 9/00* (2006.01)

(52) U.S. Cl.
CPC ............ *A61K 36/31* (2013.01); *A61K 9/0014* (2013.01); *A61K 9/0053* (2013.01); *A61K 31/192* (2013.01); *A61K 36/00* (2013.01)

(58) Field of Classification Search
CPC ...................................................... A61K 36/00
USPC ....................................................... 424/725
See application file for complete search history.

(56) References Cited

U.S. PATENT DOCUMENTS

| | | |
|---|---|---|
| 5,766,575 A | 6/1998 | Crotty et al. |
| 9,125,887 B2 | 9/2015 | Guthrie et al. |
| 2002/0090404 A1 | 7/2002 | Guthrie et al. |
| 2002/0090405 A1 | 7/2002 | Guthrie et al. |
| 2003/0072726 A1 | 4/2003 | Banister et al. |
| 2007/0098824 A1 | 5/2007 | Guthrie et al. |
| 2007/0166251 A1 | 7/2007 | Dayan et al. |
| 2007/0274937 A1 | 11/2007 | Dal Farra et al. |
| 2009/0317341 A1 | 12/2009 | Madison |
| 2010/0143275 A1 | 6/2010 | Guthrie et al. |
| 2014/0213652 A1 | 7/2014 | Guthrie et al. |

FOREIGN PATENT DOCUMENTS

| | | |
|---|---|---|
| EP | 1967175 | 9/2008 |
| FR | 2869228 A1 | 10/2005 |
| WO | WO-02/22145 A2 | 3/2002 |
| WO | WO-02/22146 A2 | 3/2002 |
| WO | WO-2007/049137 A2 | 5/2007 |
| WO | WO-2014/118610 | 8/2014 |

OTHER PUBLICATIONS

U.S. Appl. No. 13/755,143, in the U.S. Patent and Trademark Office, Office Action dated Nov. 8, 2017.
In the U.S. Patent and Trademark Office, Final Office Action in re: U.S. Appl. No. 11/260,758, dated Feb. 8, 2008, 10 pages.
In the U.S. Patent and Trademark Office, Final Office Action in re: U.S. Appl. No. 11/260,758, dated Mar. 6, 2009, 13 pages.
In the U.S. Patent and Trademark Office, Final Office Action in re: U.S. Appl. No. 13/755,143, dated Oct. 3, 2014, 15 pages.
In the U.S. Patent and Trademark Office, Notice of Allowance in re: U.S. Appl. No. 12/555,568, dated Jan. 30, 2015, 7 pages.
In the U.S. Patent and Trademark Office, Notice of Allowance in re: U.S. Appl. No. 12/555,568, dated Jun. 1, 2015, 7 pages.
In the U.S. Patent and Trademark Office, Notice of Allowance in re: U.S. Appl. No. 12/555,568, dated Mar. 3, 2014, 11 pages.
In the U.S. Patent and Trademark Office, Office Action in re: U.S. Appl. No. 11/260,758, dated Jul. 11, 2007, 8 pages.
In the U.S. Patent and Trademark Office, Office Action in re: U.S. Appl. No. 11/260,758, dated Jun. 16, 2008, 11 pages.
In the U.S. Patent and Trademark Office, Office Action in re: U.S. Appl. No. 12/555,568, dated 27, 2014, 5 pages.
In the U.S. Patent and Trademark Office, Office Action in re: U.S. Appl. No. 13/755,143, dated Nov. 5, 2013, 12 pages.
In the U.S. Patent and Trademark Office, Pre-Brief Appeal Conference decision in re: U.S. Appl. No. 13/755,143, dated Apr. 17, 2015, 2 pages.
In the U.S. Patent and Trademark Office, Protest Documents filed by 3rd Party in re: U.S. Appl. No. 12/555,568, dated Jul. 6, 2010, 22 pages.
In the U.S. Patent and Trademark Office, Requirement for Restriction/Election in re: U.S. Appl. No. 11/260,758, dated Mar. 12, 2007, 6 pages.
In the U.S. Patent and Trademark Office, Requirement for Restriction/Election in re: U.S. Appl. No. 12/555,568, dated May 27, 2011, 7 pages.
In the U.S. Patent and Trademark Office, Requirement Restriction/Election in re: U.S. Appl. No. 13/755,143, dated Aug. 22, 2013, 8 pages.
Bhārata Bhaiṣajya Ratnākara—Compiled by Nagīnadāsa Chaganalāla Śaha, Translated by Gopinath Gupta—vol. IV: B. Jain Publishers, New Delhi, 2nd Ed., Reprint, Aug. 1999. [This book contains back references from 1000 B.C.to 20th century], p. 143. (abstract only).
Cakrapānidatah; Cakradattah—Translated by Indradeva Tripathi; Chaukhamba Sanskrit Samsthan (Varanasi), 4th Ed., 2002, p. 315. (abstract only).
Cao et al., "Acyl Coenzyme a Preference of Diacylglycerol Acyltransferase from the Maturing Seeds of Cuphea, Maize, Rapeseed, and Canola," Plant Physiol., 1987: 84, pp. 762-765.
Dan-Ning et al., "Methodology for evaluation of melanin content and production of pigment cells in vitro," Photochem. Photobiol., 2008; 84(3): pp. 645-649.

(Continued)

Primary Examiner — Michael V Meller
(74) Attorney, Agent, or Firm — Porzio, Bromberg & Newman P.C.

(57) ABSTRACT

Disclosed in certain embodiments is a canola extract comprising greater than 30% sinapic acid, pharmaceutical compositions thereof, and methods thereof.

18 Claims, 8 Drawing Sheets

(56) References Cited

OTHER PUBLICATIONS

Definition of Rapeseed, from Wikipedia, the free encyclopdeia, 2007.
DeVita et al., "Combination versus single agent chemotherapy: A review of the basis for selection of drug treatment of cancer," Cancer, 1975; 35, pp. 98-110.
Economic Research Service, USDA, "Crambe, Industrial Rapeseed, and Tung Provide Valuable Oils", Industrial Uses/ IUS-6/Sep. 1996, pp. 17-23.
Hawley's Condensed Chemical Dictionary, 13th Edition, 1997, p. 204.
International Search Report for relevant International Application No. PCT/IB2014/000019, dated Apr. 16, 2014, 4 pages.
International Search Report issued in related International Application No. PCT/IB2006/003020, dated Jun. 20, 2007.
Khatlab et al., "Determination of sinapic acid derivatives in canola extracts using high-performance liquid chromatography," Journal of the American Oil Chemiste' Society, 87(2), 2010: pp. 147-155.
Kozlowski et al., "Chapter 11: Phenotic Acids and Tannins in Rapeseed and Canola," In Chemistry, Analysis, and Nutritional Effects, published by Van Nostrand Reinhold; 1990, pp. 193-197, 201-202, 205, 207 and 209.
Mohammad Najmul Ghani Khan; Khazaain-al-Adiva, vol. II (20th century AD), Nadcem Yunus Printer / Sheikh Mohd Basheer & Sons, Lahore, 1911, p. 781. (abstract only).
Mohammad Najmul Ghani Khan; Qaraabaadeen Najm-al-Ghani (20th century AD), Munshi Nawal Kishorc, Lucknow, (Second Edition), 1928, p. 34. (abstract only).
Nydahl et al., Journal of the American College of Nutrition, 1995: 14(6), pp. 643-651.
So?hala; Gadanigraha? ed,Ganga Sahaya Pandeya & Com.—Indradeva Tripathi, Part-3(Salakya-Pancakar ma Khanda) Chaukhamba Sanskrit Sansthan (Varanasi), 3rd Ed., 1999, p. 394. (abstract only).
So?hala; Gadanigraha? ed,Ganga Sahaya Pandeya & Com.—Indradeva Tripathi, Part-3(Salakya-Pancakar ma Khanda) Chaukhamba Sanskrit Sansthan (Varanasi), 3rd Ed., 1999, p. 395. (abstract only).
Sun et al., "Acyl Coenzyme a Preference of the Glycerol Phosphate Pathway in the Microsomes from the Maturing Seeds of Palm, Maize, and Rapeseed," Plant Physiol., 1988: 88, pp. 56-60.
Va?gasena; Va?gasena—Commentator Shaligram Vaisya, Edited Shankar Ialji Jain; Khemraj Shrikrishna Das Prakashan; Bombay, Ed. 1996, p. 637. (abstract only).
U.S. Appl. No. 13/755,143, Final Office Action dated Jul. 14, 2016 in the U.S. Patent and Trademark Office.
U.S. Appl. No. 13/755,143, Office Action dated Jan. 7, 2016 in the U.S. Patent and Trademark Office.
"Anti-Melasma Whitening Essence," Database GNPD, URL: <http://www.gnpd.com>, Mintel, Jun. 2011.
European Supplementary Search Report in EP 14746867.2, dated Jul. 6, 2016.
Stulberg, "Common hyperpigmentation disorders in adults: Part II. Melanoma, seborrheic keratoses, acenthosis nigricans, melasma, diabetic dermopathy, tinea versicolor," American Family Physician, 2003, [online], [retrieved on Dec. 17, 2015]. Retrieved from the Internet: <URL: http://66.197.58.78/ringworm_article_8.htm>.

CANOLA EXTRACTS CONTAINING HIGH LEVELS OF PHENOLIC ACIDS

RELATED APPLICATIONS

This application is a continuation of U.S. patent application Ser. No. 12/555,568, filed Sep. 8, 2009, which is a continuation of U.S. patent application Ser. No. 11/260,758, filed Oct. 27, 2005, the contents of which is incorporated herein by reference in their entirety.

BACKGROUND

Skin cancer is the most commonly occurring cancer, accounting for 40% of all new cancer diagnoses and for about 2% of all cancer deaths (1). It is a disease in which cancer (malignant) cells are found in the outer layers of the skin.

There are three main types of skin cancer:
a) Non-melanoma-common types such as basal cell carcinoma (BCC) and squamous cell carcinoma (SCC).
b) Melanoma-rare type, found in the cells that color the skin (melanocytes).
c) Actinic keratosis, pre-malignant skin lesion, often progresses to squamous cell cancer.

The incidence of melanoma and non-melanoma skin cancer appears to be increasing (2, 3), although melanoma incidence rates may have stabilized in the 1990s (4). Epidemiological evidence suggests that aging population, exposure to ultraviolet (UV) radiation and the sensitivity of an individual's skin to UV radiation are risk factors for skin cancer, although the type of exposure (high-intensity intermittent versus chronic) and pattern of exposure (continuous versus intermittent) may differ among the three main types of skin cancer (2, 3, 5).

Cancer is a disease of inappropriate tissue accumulation. Chemotherapeutic agents share one characteristic: they are usually more effective in killing or damaging malignant cells than normal cells. However the fact that they do harm normal cells indicates their potential for toxicity. Animal tumor investigations and human clinical trials have shown that drug combinations produce higher rates of objective response and longer survival than single agents. Combination drug therapy is therefore, the basis for most chemotherapy employed at present (DeVita, V. T. et al., 1975, Cancer 35:98).

Cancer treatment requires inhibitions of a variety of factors including tumor cell proliferation, metastatic dissemination of cancer cells to other parts of the body, invasion, tumor-induced neovascularization, and enhancement of host immunological responses and cytotoxicity. Conventional cancer chemotherapeutic agents have often been selected on the basis of their cytotoxicity to tumor cells. However, some anticancer agents have adverse effects on the patients immune system. Thus, it would be greatly advantageous if a cancer therapy or treatment could be developed that would afford non-cytotoxic protection against factors that might lead to progression of tumors. By virtue of the present invention, it has been discovered that canola extracts can be utilized to inhibit the proliferation of cancer cells.

Canola is a cruciferous crop which is mainly utilized for its extracted oil. After the oil has been extracted a protein rich meal remains which is used as a ruminant in animal diets. Further extraction of the canola meal yields minor components from canola, including, glucosinolates, phenolic acid esters and phenolic acids. The total content of selected minor components in Canola extracts from prior art methods are listed below:

|  | μM/g extract | mg/g extract |
|---|---|---|
| Progoitrin | 8.52 | 3.45 |
| Gluconapin | 5.89 | 2.29 |
| 4-hydroxybrassicin | 3.22 | 1.55 |
| Glucobrassicanapin | 0.90 | 0.36 |
| Glucoalyssin | 0.64 | 0.27 |
| Napoleiferin | 0.54 | 0.23 |
| Glucobrassicin | 0.40 | 0.19 |
| Glucoraphanin | 0.22 | 0.09 |
| Sinigrine | 0.19 | 0.07 |
| Gluconasturtin | 0.19 | 0.08 |
| Neoglucobrassicin | 0.06 | 0.03 |
| 4-methoxyglucobrassicin | traces | — |

Glucosinolates present in the extract from prior art methods from flaked, cooked canola seeds are listed below:

|  | mg/g extract | % content |
|---|---|---|
| Total glucosinolates (flaked, cooked Canola seeds) | 8.61 | 0.9% |
| Total phenolic acids (flaked, cooked Canola seeds) | 134.00 | 13.4% |
| Total phenolic acids (Canola meal) | 53.15 | 5.3% |
| Free phenolic acids (Canola meal extract after hydrolysis) | 246.64 | 24.7% |

*The remaining components of extracts are mostly sugars and small amounts and saponins Content of phenolic acids in the extract from prior art methods from canola meal (mg/g extract) are listed below:

|  | Protocatechuic | Caffeic | p-coumaric | Ferulic | Sinapic |
|---|---|---|---|---|---|
| Free phenolic acids | Trace | 0.03 | 0.02 | 0.02 | 1.03 |
| Phenolic acids liberated from soluble esters | Trace | 0.07 | 0.08 | 0.56 | 50.75 |
| Phenolic acids liberated from soluble glycosides | — | Trace | 0.06 | 0.01 | 0.52 |

Content of free phenolic acids in the extract from canola meal after hydrolysis according to prior art methods (ng/g extract) are listed below:

| Protocatechuic | Caffeic | p-coumaric | Ferulic | Sinapic |
|---|---|---|---|---|
| Trace | 0.11 | 0.81 | 3.64 | 242.08 |

Content of phenolic acids in flaked, cooked canola seeds according to prior art methods (mg/g extract) are listed below:

|  | Protocatechuic | Caffeic | p-coumaric | Ferulic | Sinapic |
|---|---|---|---|---|---|
| Free phenolic acids | Trace | Trace | Trace | 0.02 | 1.18 |
| Phenolic acids liberated from soluble esters | Trace | 0.01 | 0.07 | 0.52 | 131.95 |
| Phenolic acids liberated from soluble glycosides | — | Trace | Trace | Trace | 0.25 |

U.S. Patent Application 20020090405 describes the use of canola extracts useful in inhibiting cell proliferation in at least one form of cancer. The canola extracts described therein do not contain more than about 24% sinapic acid content.

In addition to their role in the treatment of cancer, canola extracts may also be useful in the treatment of hyperlipidemias. The hyperlipidemias include six types of inheritable hyperlipoproteinemias; these types frequently are referred to as lipoprotein phenotypes. The major plasma lipids, including cholesterol and the triglycerides do not circulate freely in solution in plasma, but are bound to proteins and transported as macromolecular complexes called lipoproteins. The major lipoprotein phenotypes are chylomicrons, very low-density (pre-β) lipoproteins (VLDL), low-density (β-) lipoproteins (LDL), and high-density (α-) lipoproteins (HDL). Chylomicrons, the largest lipoproteins, carry exogenous glyceride from the intestine via the thoracic duct to adipocytes and muscle cells. VLDL carry endogenous glyceride primarily from the liver to adipocytes and muscle cells. VLDL is the main source of plasma LDL. Classification of inherited hyperlipoproteinemias according to phenotype is important, since dietary management and drug therapy are largely dependent on this information. (*The Merck Manual*, 16$^{th}$ edition, Robert Berkow and Andrew J. Fletcher, Merck & Co., Inc., Rahway, N.J. 1992).

U.S. Patent Application 20020090404 describes the use of canola extracts useful in treating hyperlipidemia. The canola extracts described therein do not contain more than about 24% sinapic acid content.

There exists a need in the art for canola extracts which are more potent than canola extracts known in the art for treating cancer and/or hyperlipidemia

OBJECTS AND SUMMARY OF THE INVENTION

It is an object of certain embodiments of the present invention to provide a canola extract comprising greater amount of sinapic acid than extracts known in the art.

It is an object of certain embodiments of the present invention to provide a canola extract which is more potent than extracts known in the art to inhibit the proliferation of at least one form of cancer.

It is an object of certain embodiments of the present invention to provide a topical pharmaceutical formulation comprising a canola extract.

It is an object of certain embodiments of the present invention to provide a topical sunscreen formulation comprising a canola extract.

It is an object of certain embodiments of the present invention to provide an oral pharmaceutical formulation comprising a canola extract.

It is an object of certain embodiments of the present invention to provide methods of treating or preventing at least one form of skin cancer comprising topically administering a pharmaceutical formulation comprising a canola extract.

It is an object of certain embodiments of the present invention to provide methods of treating or preventing at least one form of cancer comprising orally administering a pharmaceutical formulation comprising a canola extract.

It is an object of certain embodiments of the present invention to provide methods of treating hyperlipidemia comprising orally administering a pharmaceutical formulation comprising a canola extract.

It is an object of certain embodiments of the present invention to provide methods of preventing or minimizing sunburn comprising topically administering a sunscreen formulation comprising a canola extract.

It is an object of certain embodiments of the present invention to provide methods of producing the canola extracts disclosed herein.

Certain of the above objects of the invention are met by the present invention, which in certain embodiments is directed to canola extract comprising greater than 30% sinapic acid.

Certain embodiments of the present invention are directed to a canola extract having an IC$_{50}$ concentration for the inhibition of SK-MELS cell proliferation of from about 100 μg/mL to about 200 μg/mL.

Certain embodiments of the present invention are directed to a topical pharmaceutical formulation comprising a canola extract comprising greater than 30% sinapic acid and a pharmaceutically acceptable carrier suitable for topical administration.

Certain embodiments of the present invention are directed to a topical pharmaceutical formulation comprising an amount of canola extract to provide from about 0.1% to about 5% sinapic acid and a pharmaceutically acceptable carrier suitable for topical administration.

Certain embodiments of the present invention are directed to a topical sunscreen formulation comprising a sunblocking agent, a canola extract, and a pharmaceutically acceptable carrier suitable for topical administration.

Certain embodiments of the present invention are directed to a method of treating or preventing at least one form of skin cancer comprising topically administering an effective amount of a canola extract disclosed herein.

Certain embodiments of the present invention are directed to a method of treating or preventing at least one form of skin cancer comprising topically administering an effective amount of a pharmaceutical formulation disclosed herein.

Certain embodiments of the present invention are directed to a method of treating or preventing at least one form of cancer comprising orally administering an effective amount of a pharmaceutical formulation disclosed herein.

Certain embodiments of the present invention are directed to a method of preventing or minimizing sunburn comprising topically administering an effective amount of a topical sunscreen formulation disclosed herein.

Certain embodiments of the present invention are directed to a method of treating or preventing hyperlipidemia comprising orally administering an effective amount of a pharmaceutical formulation disclosed herein.

Certain embodiments of the present invention are directed to a method for extracting phenolic acids from canola meal comprising (a) homogenizing the canola meal; and (b) evaporating the homogenized mixture to dryness.

Certain embodiments of the present invention are directed to a method for extracting phenolic acids from canola meal comprising (a) mixing canola meal containing phenolic acid esters in a solvent; (b) hydrolyzing the phenolic acid esters with a base; (c) acidifying the mixture; and (d) freeze drying the mixture to obtain an extraction.

Certain embodiments of the present invention are directed to a method for extracting phenolic acids from canola meal comprising (a) mixing canola meal containing phenolic acid esters in a solvent; (b) hydrolyzing the phenolic acid esters with a base; (c) acidifying the mixture; and (d) extracting phenolic acid with a second solvent consisting essentially of ethyl acetate.

DETAILED DESCRIPTION OF THE INVENTION

In certain embodiments, the present invention is directed to a canola extract comprising at least 30% sinapic acid, preferably at least 40% sinapic acid, and most preferably at least 50% sinapic acid.

In certain embodiments, the present invention is directed to a canola extract comprising from about 40% to about 60% sinapic acid; or about 45% to about 55% sinapic acid.

In certain embodiments, the present invention is directed to a canola extract having an $IC_{50}$ concentration for the inhibition of SK-MELS cell proliferation of from about 100 µg/mL to about 200 µg/mL; from about 120 µg/mL to about 180 µg/mL; from about 100 µg/mL to about 150 µg/mL; from about 120 µg/mL to about 150 µg/mL; or from about 124 µg/mL to about 143 µg/mL.

In certain embodiments, the present invention is directed to a topical pharmaceutical formulation comprising a canola extract comprising greater than 30% sinapic acid, greater than 40% sinapic acid, or greater than 50% sinapic acid; and a pharmaceutically acceptable carrier suitable for topical administration.

In certain embodiments, the present invention is directed to a topical pharmaceutical formulation comprising a canola extract comprising from about 40% to about 60% sinapic acid, or from about 45% to about 55% sinapic acid; and a pharmaceutically acceptable carrier suitable for topical administration.

In certain embodiments, the present invention is directed to a topical pharmaceutical formulation comprising an amount of canola extract to provide from about 0.1% to about 5%, from about 0.2% to about 2.5% sinapic acid, or from about 0.4% to about 0.8% sinapic acid; and a pharmaceutically acceptable carrier suitable for topical administration.

In certain embodiments, the present invention is directed to a topical pharmaceutical formulation comprising from about 0.1% to about 5% sinapic acid, from about 0.2% to about 2.5% sinapic acid, or from about 0.4% to about 0.8% sinapic acid; and a pharmaceutically acceptable carrier suitable for topical administration.

In certain embodiments, the topical pharmaceutical formulation of the present invention is selected from the solution, a suspension, an emulsion, a lotion, an ointment, a gel, a cream, or an oil.

In certain embodiments, the invention is directed to a transdermal delivery system comprising a transdermal delivery device and a topical pharmaceutical formulation as disclosed herein. In certain embodiments, the transdermal delivery device is selected from the group consisting of a transdermal patch, a transdermal plaster, a transdermal disc and an iontophoretic transdermal device.

In certain embodiments, the present invention is directed to a topical sunscreen formulation comprising a sunblocking agent, a canola extract, and a pharmaceutically acceptable carrier suitable for topical administration.

In the topical sunscreen formulations of the present invention, the sunblocking agent can be selected from the group consisting of oxybenzone, sulisobenzone, dioxybenzone, menthyl anthranilate, para aminobenzoic acid (PABA), octyl methoxycinnamate, octocrylene, drometrizole trisiloxane, octyl salicylate, homomenthyl salicylate, octyl dimethyl PABA, TEA salicylate, butylmethoxy dibenzoylmethane (avobenzone), 4-methyl benzylidene camphor, 3-benzylidene camphor, benzylidene camphor sulfonic acid, octyl triazone, terephthalydiene dicamphor sulfonic acid, ethyl PABA, hydroxy methylphenyl benzotriazole, methylene bis-benzotriazoyltetramethylbutylphenol, diethylhexyl-2,6-naphthalate, di-t-butyl hydroxybenzylidene camphor, bis-ethylhexyloxyphenol methoxyphenol triazine, titanium dioxide, zinc oxide, and any combinations thereof.

In certain embodiments, the sunblocking agent is present at up to about 70 wt %, at about 0.05 wt % to about 50 wt %, or at about 0.5 wt % to about 30 wt %, based on the total weight of the formulation.

In certain embodiments, the sunscreen formulation exhibits an SPF of about 2 to about 70, or from about 15 to about 45.

In certain embodiments, the present invention is directed to an oral pharmaceutical formulation comprising a canola extract comprising at least 30% sinapic acid, preferably at least 40% sinapic acid, and most preferably at least 50% sinapic acid; and a pharmaceutically acceptable excipient.

In certain embodiments, the present invention is directed to an oral pharmaceutical formulation comprising a canola extract comprising from about 40% to about 60% sinapic acid, or from about 45% to about 55% sinapic acid; and a pharmaceutically acceptable excipient.

In certain embodiments, the oral pharmaceutical formulation is in the form a liquid, a tablet, a capsule, a gelcap, or a powder.

The canola extract of the present invention can be incorporated into the formulations of the present invention in an amount to provide the desired pharmacodynamic action (i.e., an anti-proliferative effect, or antihyperlipidemic effect). The concentration can be, e.g. from about 0.01 µg/ml to about 10000 µg/ml. This range is not meant to be limiting as one skilled in the art would be able to determine the effective concentration range to provide the desired effect.

In certain embodiments, the composition of canola extract comprises a dose of phenolic acids to provide, e.g., a concentration from about 0.1 µg/ml to about 1000 µg/ml, from about 125 µg/ml to about 600 µg/ml, from about 250 µg/ml to about 600 µg/ml or from about 400 µg/ml to about 600 µg/ml.

In certain embodiments, the composition of canola extract comprises a dose of sinapic acid to provide a concentration, e.g., from about 1 µg/ml to about 500 µg/ml; from about 10 µg/ml to about 400; or from about 40 µg/ml to about 200 µg/ml.

In certain embodiments, the pharmaceutical compositions of the present invention inhibit cell proliferation of at least one form of cancer from about 25% to about 100%, preferably from about 50% to about 100% and most preferably from about 75% to about 100%.

Cancers that can be prevented and/or treated by the compositions and methods of the present invention include colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In certain embodiments, the pharmaceutical compositions of the present invention reduce elevated lipoproteins by about 25% or more, by about 50% or more or about 75% or more, depending on the individual needs of the patient.

In certain embodiments the canola extract of the present invention may also be administered with another compound capable of lowering blood levels of triglycerides, cholesterol, or glycerol, including but not limited to fibrates (e.g., bezafibrate, gemfibrozil, and clofibrate), HMG-COA reductase inhibitors (e.g., somatostatin, pravastatin, simvastatin, and fluorastatin, atorvastatin, and lovastatin), bile acid binding resins (e.g., cholestyramine and colestipol), nicotinic acid compounds (e.g., nicotinic acid and niceritrol), and fish oils. The additional compound can be administered before, with or after the canola extract.

The present invention can be administered intravenously, intraperitoneally, subcutaneously, intramuscularly, intrathecally, orally, sublingually, into the buccal cavity, rectally, topically or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

In certain embodiments, the compounds of the present invention can be administered in a local manner, for example, via injection of the compound directly into a tumor, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Furthermore, one may administer the agent in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

In certain embodiments, the present invention is directed to a method for extracting phenolic acids from canola meal comprising (a) homogenizing the canola meal; and (b) drying the homogenized mixture (e.g., by evaporation or freeze drying).

In certain embodiments, the canola meal is homogenized in menthol:water, preferably in a ratio of 5:5 to 9:1, preferably the ratio is about 7:3.

In certain embodiments, the present invention is directed to a method for extracting phenolic acids from canola meal comprising (a) mixing canola meal containing phenolic acid esters in a solvent; (b) hydrolyzing the phenolic acid esters with a base; (c) acidifying the mixture; and (d) freeze drying the mixture to obtain an extraction.

In certain embodiments, the present invention is directed to a method for extracting phenolic acids from canola meal comprising (a) mixing canola meal containing phenolic acid esters in a solvent; (b) hydrolyzing the phenolic acid esters with a base; (c) acidifying the mixture; and (d) extracting phenolic acid with a second solvent consisting essentially of ethyl acetate.

In certain embodiments, the solvent comprises methanol:water in a ratio of 5:5 to 9:1, preferably the ratio is about 7:3.

In certain embodiments, the base can be an organic or inorganic base or alkaline agent such as sodium carbonate, sodium bicarbonate, sodium phosphate dibasic, sodium phosphate tribasic, sodium citrate, magnesium hydroxide, magnesium carbonate, calcium carbonate, calcium phosphate, sodium hydroxide, tribasic phosphate, potassium phosphate and mixtures thereof. A preferred base is sodium hydroxide.

In certain embodiments, the present invention further comprises extracting phenolic acid with an alkyl acetate (preferably ethyl acetate) after acidification and resuspending the extraction is a second solvent prior to freeze drying. Preferably, the second solvent is methanol.

In certain embodiments, the present invention further comprises washing the freeze dried extraction with a third solvent. Preferably, the third solvent is hexane. In further embodiments, the extraction is filtered and dried, e.g., by evaporation.

In certain embodiments, the acidifying step is to a pH of less than 5, preferably to a pH of about 2. The acidifying step can be performed with any suitable organic or inorganic acidic material, e.g., inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like.

Example 1

Extraction of CPA (Canola Phenolic Acid) from Canola meal

The extract enriched in total phenolics was isolated from canola meal by homogenization in methanol:water, 70:30, v/v and evaporation of supernatant to dryness. According to HPLC analysis (R. Amarowicz), this extract (Phenolic Extract Saskatoon Research Centre, Agriculture and Agri-Food Centre, Apr. 24, 2002) contained 5.3% phenolic acids (Table 1).

TABLE 1

Composition of phenolic acids in the extract from canola meal (mg/g)

| | Sinapic | Ferulic | p-coumaric | Caffeic | Protocatechuic |
|---|---|---|---|---|---|
| Esters | 50.75 | 0.56 | 0.08 | 0.07 | Trace |
| Free | 1.03 | 0.02 | 0.02 | 0.03 | trace |
| Insoluble-bound | 0.52 | 0.01 | 0.06 | Trace | — |
| Total | | | 53.15 mg/g (5.3%) | | |

Figure 1:
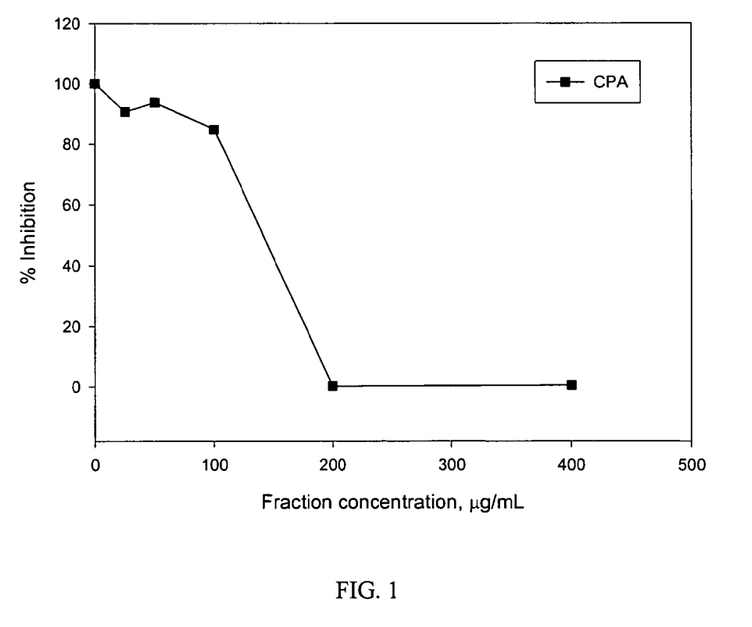
FIG. 1 is a graph depicting the inhibition of SK-MELS cell proliferation by phenolic acid enriched canola meal extract using various extraction procedures.
Figure 2A:
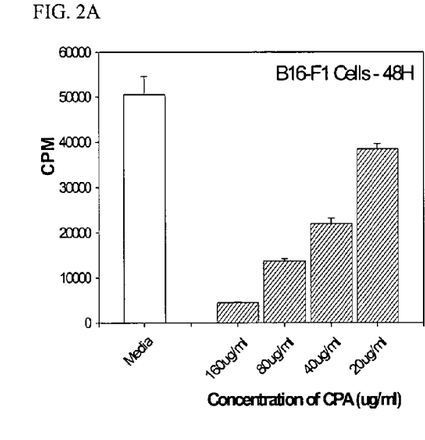
FIGS. 2A and 2B are graphs depicting in the inhibition of the proliferation of B16-F1 cells by CPA after 48 hours and 72 hours, respectively.
Figure 2B:
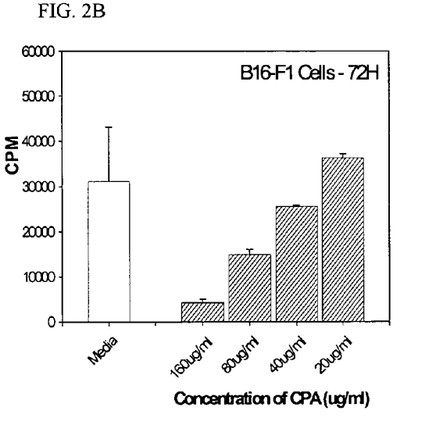
Figure 3A:
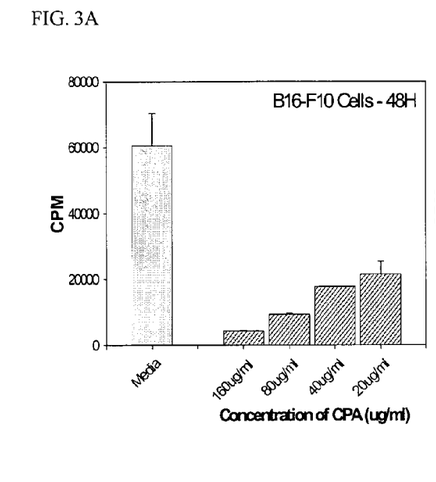
FIGS. 3A and 3B are graphs depicting the inhibition of the proliferation of B16-F10 cells by CPA after 48 hours and 72 hours, respectively.
Figure 3B:
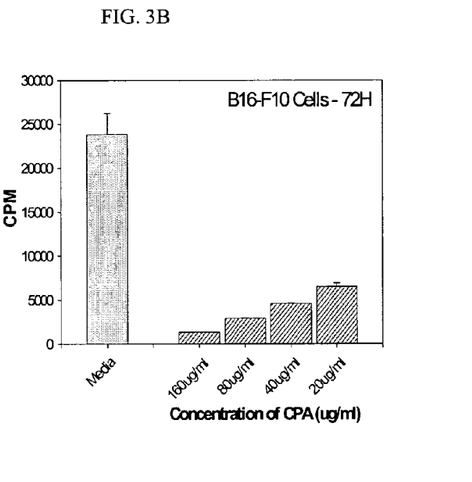

This extract from canola meal had a substantial antiproliferative activity against human skin cancer cell line SK-MELS in the Alamar Blue assay. The bioactive fraction was subsequently isolated by a large-scale procedure (developed for that purpose), tested again for anti-proliferative activity in SK-MELS cells. $IC_{50}$ concentrations (concentrations needed to inhibit cell proliferation by 50%)=140 µg/mL (FIG. 1).

The CPA extract dose-dependently inhibited the proliferation of SK-MEL-5 cells. CPA extract was tested for the antiproliferative activity in cancer cell lines using a vital stain AlamarBlue™ assay. The exponentially growing cells were harvested and seeded in 96-well plates at density $1.5 \times 10^4$ cells/mL. Plates were incubated at 37° C. for 18 hours to allow the cells to attach. The exposure to CPA extracts at various concentrations was initiated by addition of one volume of growth medium (100 µL) containing the extracts at 2 times the desired final concentrations, in triplicate wells. After 4 days of incubation, cell density was determined using AlamarBlue™ and a fluorescence-based plate reader interfaced with a computer. $IC_{50}$ concentrations (concentrations of CPA required to inhibit cell proliferation by 50%) were determined.

Example 2

In vitro Analysis

To evaluate anticancer activities of CPA, B16-F1 and B16-F10 malignant melanoma tumor cells (10,000) were cultured with CPA (solubilized in dimethyl sulfoxide, DMSO)) at 160, 80, 40 and 20 µg/ml. The cells were incubated for 72 hours in culture in presence or absence of extracts. The cells were cultured at 37° C. in 5% $CO_2$ for 48 and 72 hours. [$^3$H] thymidine was added to the cell cultures, cell proliferation was measured by [$^3$H] thymidine uptake using Micro beta-Scintillation counter. See FIGS. 2A, 2B, 3A and 3B.

Preliminary in vitro studies showed that CPA inhibited the proliferation of B16-F1 and B16-F10 malignant melanoma tumor cells for up to 72 hours in culture in a dose dependent manner.

Example 3

In vivo Analysis

Male C57BL/6 mice (17 wks old) were acclimatized for 4 days. Mice were treated for a week (oral) with CPA followed by injections of B16-F1 malignant melanoma tumor cells ($2.0 \times 10^5$) in 100 µl saline subcutaneously in the right hind flank of mice. Mice were monitored for tumor growth for 28 days from the date of injection.

a) Effect of CPA Extracts on Development of Melanoma in Mice (Oral Gavage).

Mice were given 6.0% CPA w/v of CPA in Canola oil (0.2 ml) by oral gavages daily for additional 4 weeks after tumor cell injection.

Figure 4:
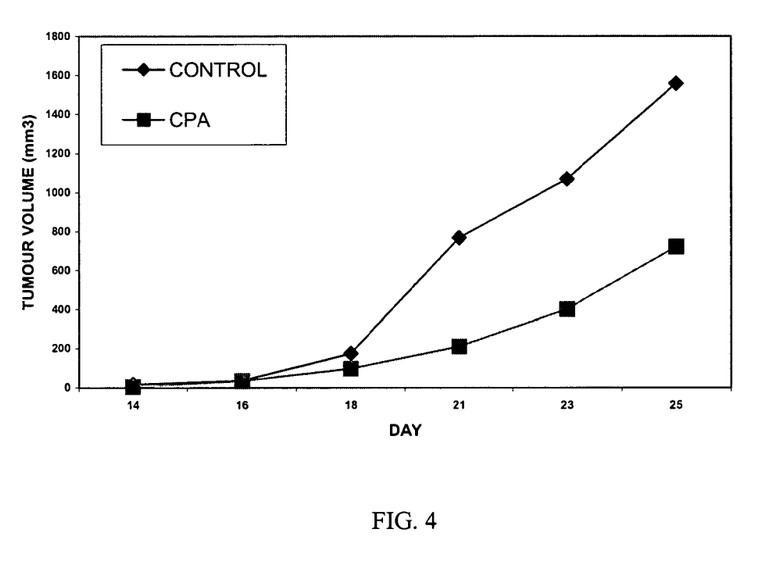
FIG. 4 is a graph depicting the change in tumor volume after treatment with CPA (oral).

Tumor Volume: When primary tumours became visible/palpable, their maximum length and width were measured and tumour volume calculated (p<0.04). It was observed that the growth of tumor was similar in mice treated with CPA by oral gavage as compared to the controls up to day 18 of treatment. After day 18, CPA treated group showed a significant reduction in the tumor volume as compared to control suggesting inhibition of tumor growth by CPA. See FIG. 4.

Figure 5:
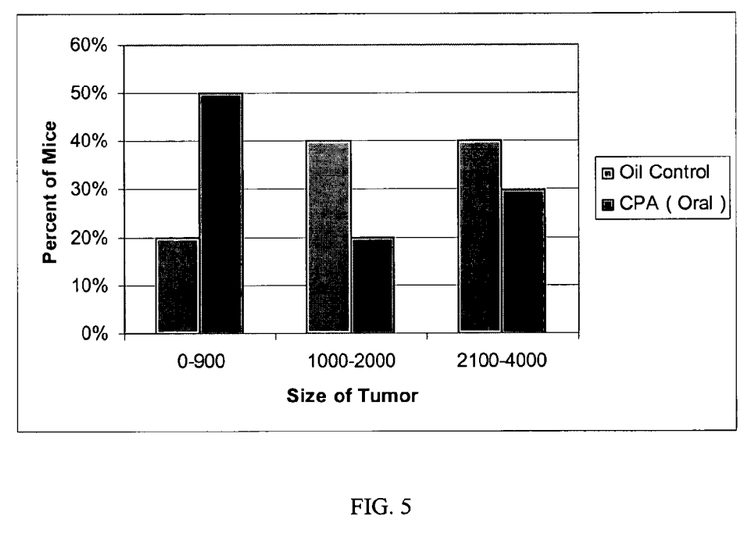
FIG. 5 is a graph depicting the change in tumor size after treatment with CPA (oral).

Tumor Size: Further, effect of CPA treatment on tumor size was analyzed. When primary tumors became visible/palpable, their maximum length and width were measured at a minimum 3 times weekly using calipers and their tumor sizes were calculated. It was observed that 50% of mice treated with CPA by oral gavage had smaller tumors (0-900) compared to the 20% of vehicle treated (control) mice. The data also showed that 80% of mice from control group had larger tumors compared to CPA treated mice. See FIG. 5.

b) Effect of CPA Extracts on Development of Melanoma in Mice (Topical Application).

Mice were treated with topical application of 6.0% CPA w/v of CPA in a cream base for an additional 4 weeks after tumor cell injection.

Figure 6:
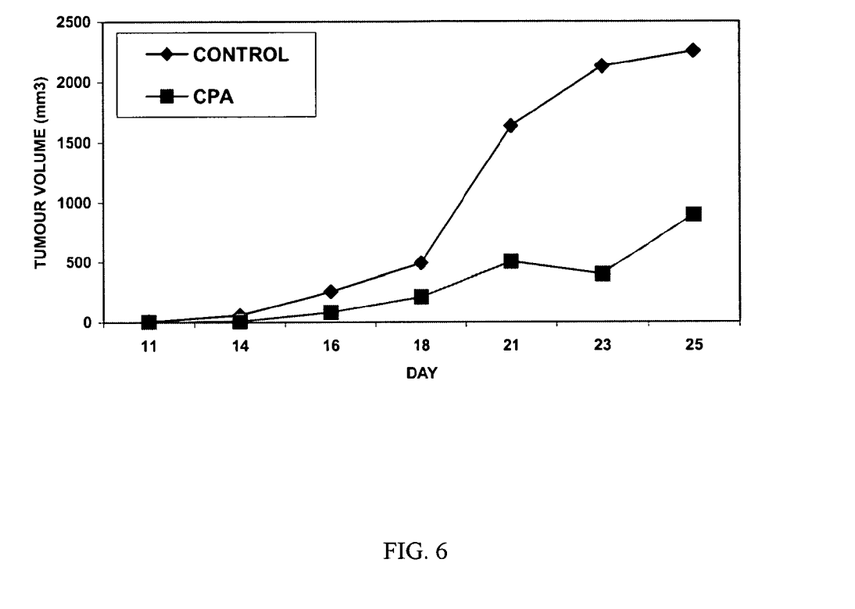
FIG. 6 is a graph depicting the change in tumor volume after treatment with CPA (topical).

Tumor Volume: It was observed that mice treated with CPA by topical application showed similar tumor volume as compared to the controls up to day 14 of treatment. When primary tumors became visible/palpable, their maximum length and width were measured and tumor volume calculated (p<0.01). After day 14 a significant reduction in the tumor volume was observed as compared to control till the end of the study. See FIG. 6.

Figure 7:
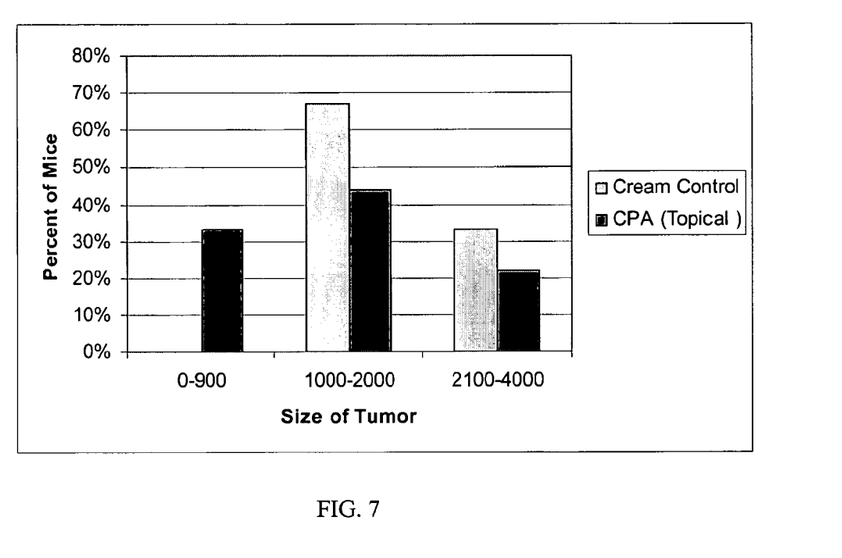
FIG. 7 is a graph depicting the change in tumor size after treatment with CPA (topical).
Figure 8:
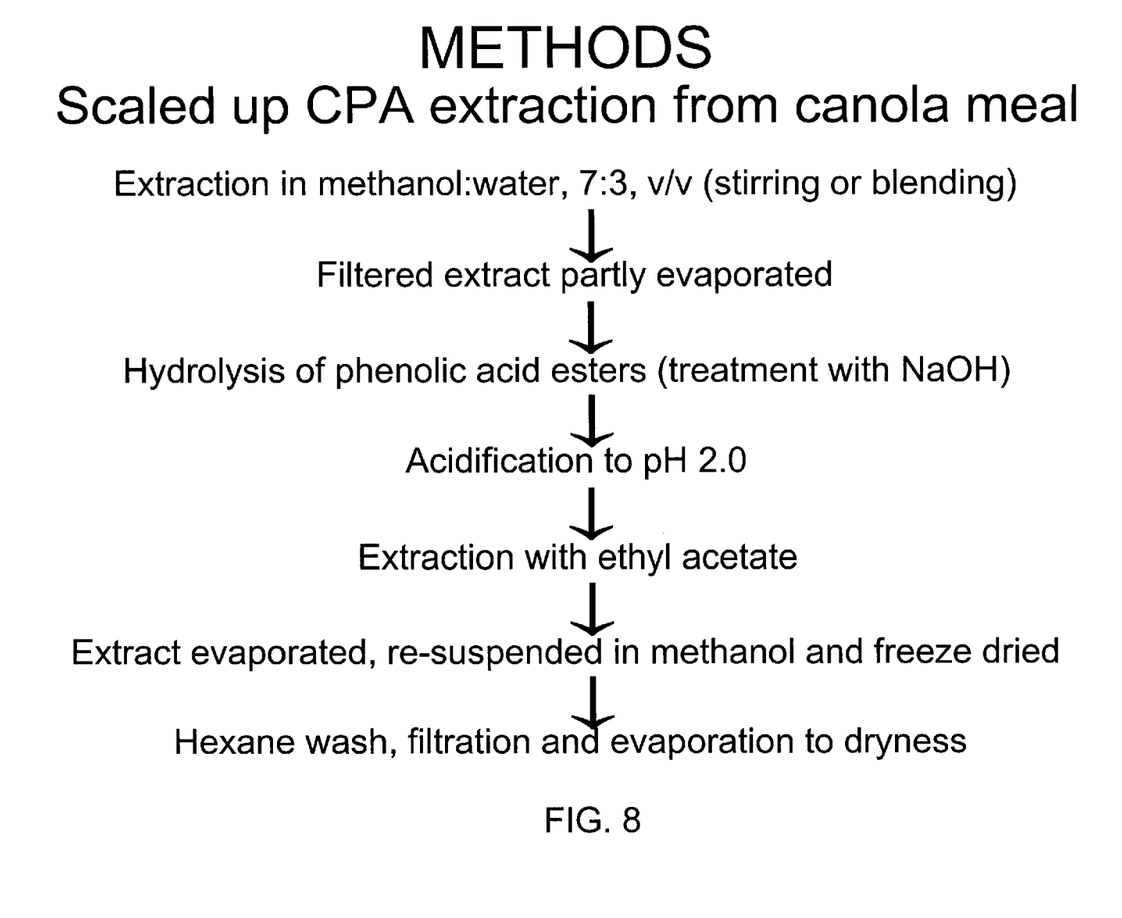
FIG. 8 is a flowchart depicting a scaled up extraction method of the present invention.

Tumor Size: When primary tumors became visible/palpable, their maximum length and width were measured at a minimum 3 times weekly using calipers and their tumor sizes were calculated. Comparison of tumor sizes between groups showed that mice (30%) treated with CPA by topical application had smaller tumors (0-900) as compared to the control mice. The control group had higher percentage of mice with larger tumors suggesting that topical application of CPA reduces the tumor size. See FIG. 7.

Discussion

Results from the above experiments show a reduction in tumor volume and size in mice treated with CPA by both oral and topical routes compared to the controls. Although the initial growth of tumors was similar in both the CPA treated and control groups, CPA treatment reduced the tumor volume and size in both the models. These results suggest that supplementation with CPA by both oral and topical routes may have beneficial effects in treating melanoma.

Conclusions

The above data suggest that CPA has antiproliferative and antineoplastic activity both in vitro and in vivo.

It is most effective against human melanoma cells.

CPA and its active constituents have the potential to treat melanoma skin cancer in mice.

No toxicity was observed in pre-clinical rodent trials.

We claim:

1. A process consisting essentially of:
administering a therapeutically effective amount of a composition for treating melanoma to a human in need thereof, the composition consisting essentially of: a canola extract comprising about 1 µg/mL to about 500 µg/mL sinapic acid and an agent selected from the group consisting of oxybenzone, dioxybenzone, octyl methoxycinnate, 3-benzylidene camphor, and combinations thereof.

2. The process of claim 1, wherein the administering is oral administration.

3. The process of claim 2, wherein the canola extract is 6.0% canola extract w/v of canola extract in canola oil.

4. The process of claim 1, wherein the administering is topical administration.

5. The process of claim 4, wherein the canola extract is 6.0% canola extract w/v of canola extract in a cream base.

6. The process of claim 1, wherein the administering is for at least one week.

7. The process of claim 6, wherein the administering is for at least four weeks.

8. The process of claim 1, wherein the administering is one a day.

9. The process of claim 1, wherein the canola extract comprises about 5.3% phenolic acids.

10. The process of claim 1, wherein the process reduces elevated lipoproteins by about 25% or more.

11. The process of claim 10, wherein the process reduces elevated lipoproteins by about 75% or more.

12. The process of claim 1, wherein the canola extract has an $IC_{50}$ concentration for the inhibition of SK-MELS cell proliferation from about 100 µg/mL to about 200 µg/mL.

13. The process of claim 12, wherein the canola extract has an $IC_{50}$ concentration for the inhibition of SK-MELS cell proliferation from about 120 µg/mL to about 150 µg/mL.

14. The process of claim 1, wherein the canola extract comprises at least 30% sinapic acid.

15. The process of claim 14, wherein the canola extract comprises at least 50% sinapic acid.

16. The process of claim 1, wherein the canola extract comprises about 40% to about 60% sinapic acid.

17. The process of claim 16, wherein the canola extract comprises about 45% to about 55% sinapic acid.

18. The process of claim 1, wherein the canola extract comprises about 40 µg/mL to about 200 µg/mL sinapic acid.

* * * * *